United States Patent
Forman et al.

(10) Patent No.: US 11,253,154 B2
(45) Date of Patent: Feb. 22, 2022

(54) METHOD AND SYSTEM FOR MAGNETIC RESONANCE IMAGING

(71) Applicants: Siemens Healthcare GmbH, Erlangen (DE); King's College London, London (GB)

(72) Inventors: Christoph Forman, Erlangen (DE); Radhouene Neji, Erlangen (DE); Karl-Philipp Kunze, Camberley (GB); Rene Botnar, London (GB); Claudia Prieto, London (GB)

(73) Assignees: Siemens Healthcare GmbH, Erlangen (DE); King's College, London, London (GB)

( * ) Notice: Subject to any disclaimer, the term of this patent is extended or adjusted under 35 U.S.C. 154(b) by 0 days.

(21) Appl. No.: 17/003,574

(22) Filed: Aug. 26, 2020

(65) Prior Publication Data
US 2021/0059529 A1    Mar. 4, 2021

(30) Foreign Application Priority Data
Aug. 27, 2019 (GB) .................................... 1912243

(51) Int. Cl.
| A61B 5/00 | (2006.01) |
| G01R 33/34 | (2006.01) |
| G01R 33/56 | (2006.01) |
| G01R 33/565 | (2006.01) |
| A61B 5/055 | (2006.01) |

(52) U.S. Cl.
CPC ............ *A61B 5/0037* (2013.01); *A61B 5/055* (2013.01); *G01R 33/34084* (2013.01); *G01R 33/5608* (2013.01); *G01R 33/56509* (2013.01)

(58) Field of Classification Search
CPC .......... G01R 33/34084; G01R 33/5608; G01R 33/56509; G01R 33/5676; G01R 33/5614; A61B 5/0037; A61B 5/055; A61B 5/7207
See application file for complete search history.

(56) References Cited

U.S. PATENT DOCUMENTS

| 4,851,777 | A | * | 7/1989 | Macovski | ............... G01R 33/54 324/309 |
| 5,257,626 | A | * | 11/1993 | Pelc | ..................... G01R 33/563 324/312 |
| 7,768,264 | B1 | | 8/2010 | Brau et al. | |
| 2007/0007960 | A1 | | 1/2007 | King et al. | |
| 2008/0297152 | A1 | | 12/2008 | Brau et al. | |

OTHER PUBLICATIONS

Parker et al., Phase Reconstruction from Multiple Coil Data Using a Virtual Reference Coil, Magn Reson Med., 72(2): 563-569. (Year: 2014).*

Henningsson, M. (2013). Prospective respiratory motion correction for coronary MR Angiography using a 2D image navigator. Magnetic Resonance in Medicine, 69, pp. 486-494; 2013.

* cited by examiner

*Primary Examiner* — Susan S Lee
(74) *Attorney, Agent, or Firm* — Schiff Hardin LLP

(57) ABSTRACT

A method and system for imaging a body using a magnetic resonance imaging (MRI) apparatus, including motion tracking of a target object of the body using MRI by generating an MRI image of a region of interest of the body by performing a weighted combination of a signal received by each coil of an MRI apparatus during an MRI scan.

15 Claims, 3 Drawing Sheets

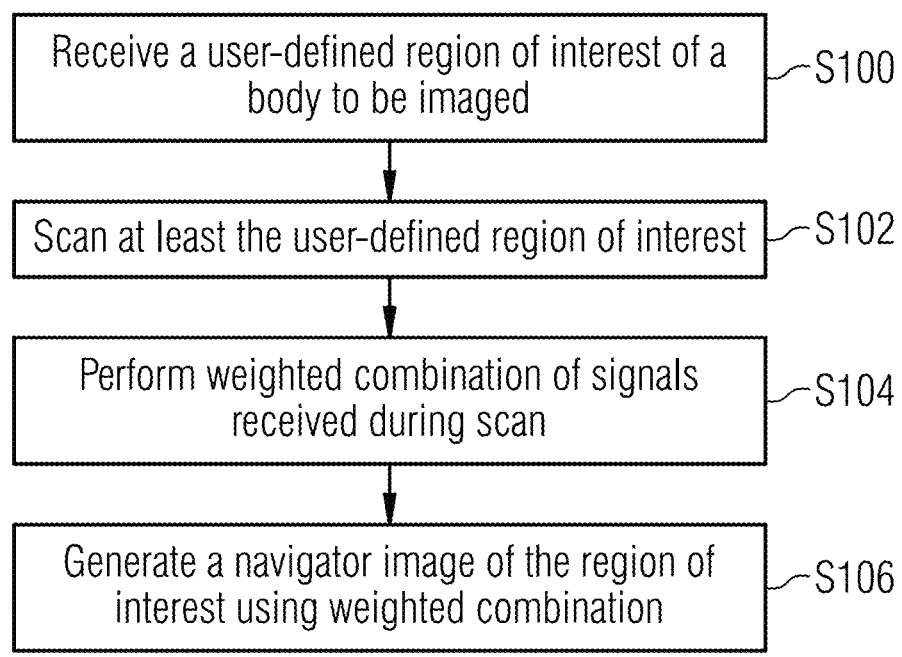

METHOD AND SYSTEM FOR MAGNETIC RESONANCE IMAGING

FIELD OF DISCLOSURE

The present techniques relate to a method and system for imaging a body using a magnetic resonance imaging (MRI) apparatus. In particular, the present techniques relate to methods for improving motion tracking of an organ of the body using MRI navigators.

BACKGROUND

Imaging the heart by coronary magnetic resonance angiography, for example, can be difficult because of patient movement—specifically respiratory motion—during the imaging process. The movement may cause artefacts to appear in the images generated during the procedure, which may make it difficult to make a diagnosis.

Existing techniques for compensating for respiratory motion involve using one- or two-dimensional navigators. Navigators are additional radio frequency pulses which are applied to dynamically track motion, such as the motion of a diaphragm and heart during breathing. The preparation pulses of a balanced steady-state free precession (bSSFP) sequence may be used to acquire low resolution navigator images in a 3D imaging sequence. The navigator images may represent a two-dimensional (2D) projection image of a 3D volume being imaged, since only phase-encoding is performed. Motion, such as that of the heart, may be tracked during the main MRI scan using a template matching algorithm relative to the navigator image obtained, for example, from a ramp-up stage for a bSSFP sequence. However, subcutaneous fat or signals from other areas of the body may overlay the region of interest, which may degrade the tracking result.

If the navigator images are obtained during a ramp-up stage during the bSSFP sequence (during which the flip angles increase from a low or zero flip angle to a final image flip angle), the navigator signals are acquired with the centre of k-space at the end of the ramp-up. This means the navigator signals are subject to a low-pass filtering effect, as higher frequencies are acquired first and then lower frequencies. This may further degrade the tracking result, as some important information or details may be removed from the navigator images as a consequence of the low-pass filtering.

Therefore, there is a desire to provide a method and system for improved motion tracking during MRI.

SUMMARY

To address these problems, the present techniques provide a method of correcting for motion in magnetic resonance images during image acquisition using a magnetic resonance imaging (MRI) apparatus comprising a plurality of coils for receiving signals, the method comprising: receiving a user-defined region of interest of a body to be imaged; scanning, using the MRI apparatus, at least the region of interest of the body; and generating a navigator image of the region of interest by performing a weighted combination of a signal received by each coil during the scanning.

Existing techniques for tracking and correcting for motion during MRI may involve creating a 2D navigator image by performing a sum-of-squares combination of all the signals received by the coils of an MRI apparatus during the preparation pulses of the bSSFP sequence.

Typically during an MRI scan, the contribution of signals from all coils are combined to generate an MRI image. The present techniques improve upon this technique by performing a weighted combination of all the coils of the MRI apparatus, based on a user-defined region of interest of the body. For example, the region of interest may be around the heart. The weighted combination means that coils that provide a greater contribution to imaging in the region of interest are weighted higher, while coils that make a lesser contribution to imaging in the region of interest are weighted lower, or are not used at all to generate an MRI image of the region of interest. This weighted combination technique enhances the signal from a target object (e.g., the heart) in the region of interest in the MRI image, and reduces the signal from other objects in the region, or from objects outside of the region. This technique also improves the motion tracking of the target object.

In a particular example of performing a weighted combination, the signals received by certain coils (e.g., the coils nearest the spine) may be weighted with a weighting of 1 and signals received by all other coils may be weighted with a weighting of 0, to thereby avoid signals originating from subcutaneous fat or the chest wall. It will be understood that this is a particular example, and in other cases, the coils may be assigned any weighting value.

The method of imaging may further comprise determining a weighted contribution of each coil of the plurality of coils to a navigator image of the region of interest. Two techniques for determining how to weight the signal contributions from each coil are now described. These weights may be a first set of weights used to generate a navigator image, and may be coil-dependent weights. It will be understood that these are examples and other techniques may be employed.

One technique for determining how to weight the signal contributions from each coil comprises knowing the coil geometry of the coils of the MRI apparatus. Thus, the step of determining a weighted contribution of each coil may comprise: obtaining a coil geometry of the plurality of coils; determining, using the coil geometry, a distance of each coil from the region of interest; and assigning a weight to each coil based on the determined distance of each coil from the region of interest. The region of interest may be defined by a set of coordinates, and these may be mapped to the coil geometry to determine which coils are within the region of interest, close to the region of interest or far from the region of interest. This may then be used to assign a weight to each coil based on the determined distance of each coil from the region of interest. For example, a high weight may be assigned to each coil which is close to the region of interest, because a signal received from a coil that is in or close to the region of interest may be desirable to generate an accurate representation of a target object in the region. Similarly, a low weight may be assigned to each coil which is further away from the region of interest, because a signal received from a coil that is further away from the region of interest may obscure the target object.

Another technique for determining how to weight the signal contributions from each coil comprises knowing the coil sensitivity or coil sensitivity profiles of the coils of the MRI apparatus. Thus, the step of determining a weighted contribution of each coil may comprise: performing a prescan, using the MRI apparatus, over at least the region of interest of the body; determining, using the prescan, a coil sensitivity of each coil in the region of interest; and assigning a weight to each coil based on the determined coil sensitivity. The step of determining a coil sensitivity of each coil in the region of interest may comprise: assigning a high sensitivity to each coil which produces a bright image in the prescan of the region of interest; and assigning a low sensitivity to each coil which produces a dim image in the prescan of the region of interest. Thus, the step of assigning a weight to each coil based on the determined coil sensitivity in the region of interest may comprise: assigning a high weight to each high sensitivity coil in the region of interest; and assigning a low weight to each low sensitivity coil in the region of interest.

The step of generating a navigator image of the region of interest may be performed in real-time during the scan, in an instance when the weighted contribution of each coil is known prior to the scanning. For example, if the prescan is performed ahead of the main MRI scan, the weighted contributions may also be determined before the main MRI scan, such that the signals received during the main MRI scan may be combined in real-time using the known weighted contributions. Similarly, if the coil geometry is known, the weighted contributions may also be known, and therefore, the navigator signals received during the main MRI scan may be combined in real-time using the known weighted contributions.

Alternatively, the step of generating a navigator image of the region of interest may be performed after the scanning is complete. In this case, the weighted contributions of each coil may be used to perform a weighted contribution of the signals received during the main MRI scan after the scan is complete.

As mentioned above, performing a prescan may comprise performing a separate scan prior to performing the scan for actual data acquisition (that is, prior to the main MRI scan). The prescan may be performed only once at the beginning of an MRI procedure, and may not be performed again even if, for example patient position within the apparatus changes. The navigator image may be acquired during the scanning step. Thus, the scanning step may comprise: applying ramp-up preparation pulses for a balanced steady-state free precession scan; and obtaining low resolution navigator images of at least the region of interest while the ramp-up preparation pulses are applied. The low resolution navigator images may be one-dimensional images, two-dimensional images, or three-dimensional images.

Thus, the step of performing a weighted combination of a signal received by each coil during the scanning may comprise performing a weighted combination of signals using a first set of weights to remove any unwanted signals when generating the navigator image.

The step of generating a navigator image of the region of interest may comprise applying a second set of weights which counteract the low-pass filtering that occurs when the signals for the navigator images are being acquired. Thus, while the first set of weights described above remove any unwanted signal (and are therefore coil-dependent weights), the second set of weights counteract the variable flip angles/ low-pass filtering effect (and are therefore, coil-independent weights).

The low resolution navigator images may be low-pass filtered images. Thus, generating the navigator image may comprise performing two steps or applying two sets of weights. Firstly, the navigator images may be generated by using the weighting of each coil to remove any unwanted signal from the image, that is, to only generate the navigator images using signals from the coils that are in or close to the region of interest. These weights may be coil dependent, and may be determined based on, for example, the coil sensitivity or coil geometry mentioned above. Secondly, the navigator images may be generated using weights that remove the low-pass filtering effect, that is, to counteract the effect of the variable flip angles that are applied during the bSSFP ramp. These weights may be determined by knowing how the bSSFP ramp is applied and how the flip angles vary during the ramp. The two sets of weights may be combined such that a single set of weights is used to generate the navigator image.

Thus, the weights may be chosen to remove unwanted signal and/or remove the low-pass filtering effect.

Thus, the step of performing a weighted combination of a signal may comprise performing a weighted combination of signals using a second set of weights to remove low-pass filtering when generating the navigator image.

However, the weights may also be chosen to reverse the initial low-pass filtering modulation to produce a high-pass filtering effect instead. The step of performing the weighted combination of signals may therefore comprise performing a weighted combination of signals using a third set of weights to reverse the low-pass filtering when generating the navigator image of the region of interest, thereby generating a high-pass filtered navigator image. This technique may produce an improvement in edge detection in the main navigator image, which may lead to significantly better motion tracking, particularly in the left-right direction.

The weights used to generate a navigator image may be the combination of the first set of weights (coil-dependent) and the second set of weights (coil-independent)—this may remove unwanted signals and remove the low-pass filtering. Alternatively, the weights used to generate a navigator image may be the combination of the first set of weights (coil-dependent) and the third set of weights (coil-independent)—this may remove unwanted signals and reverse the low-pass filtering.

The present techniques also provide a (non-transitory) computer readable medium carrying processor control code which when implemented in a system (e.g., an image processor) causes the system to carry out the methods described herein.

The present techniques also provide an image processing system for processing an image. The system may comprise an image processor which is configured to carry out the methods described herein. The system may also comprise an image capture device which is configured to capture an image, and this is the input image which may be received by the image processor. The system may also comprise a user interface which is configured to display an output result generated by the image processor.

BRIEF DESCRIPTION OF THE DRAWINGS

The above mentioned attributes and other features and advantages of this disclosure and the manner of attaining them will become more apparent and the disclosure itself will be better understood by reference to the following description of embodiments of the disclosure taken in conjunction with the accompanying drawings, wherein:

FIG. 1 shows a flowchart of example steps of imaging using an MRI apparatus;

DETAILED DESCRIPTION

Figure 2A:
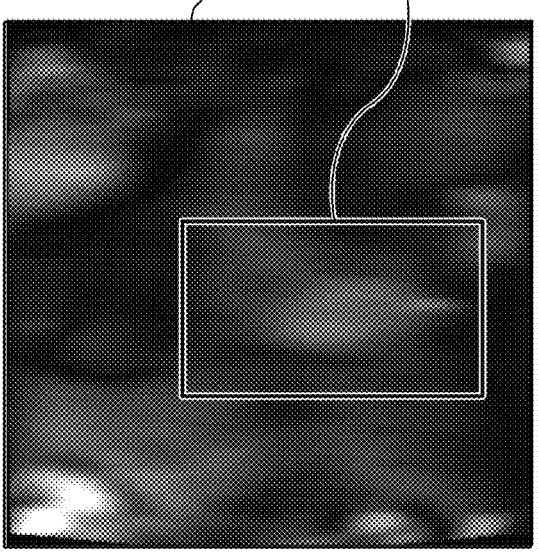
FIG. 2A shows an example MRI navigator image produced using a sum-of-squares combination of all coils.

FIG. 1 shows a flowchart of example steps of correcting for motion in MRI images during image acquisition using an MRI apparatus that comprises a plurality of coils for receiving signals. The process begins by receiving a user-defined region of interest of or on a body to be imaged (step S100). For example, a user of the MRI apparatus may input a region of interest via a user interface. The region of interest may be input as a box around a target object, such as a patient's heart. A much larger area of the patient than the region of interest may be scanned using the MRI apparatus. However, the region of interest may be used to determine how to combine the signals received by the plurality of coils to generate the MRI image of the region of interest (or target object therein).

Once the region of interest has been defined, the process may comprise performing an MRI scan of at least the user-defined region of interest (step S102).

The signals received by the plurality of coils during the MRI scan may then be combined using a weighted combination (step S104). This may comprise determining a weighted contribution of each coil of the plurality of coils to a navigator image of the region of interest. The weighted combination of signals may improve the image quality of the navigator images in two ways. Firstly, the image quality may be improved by removing or reducing signals received from coils that are outside of or far from the user-defined region of interest, or from features which obscure the image (e.g., subcutaneous fat). As mentioned above, the weights applied to the signals to remove/reduce unwanted signals may be coil-dependent weights (obtained by knowing the coil sensitivities or coil geometries, potentially by performing a prescan). Secondly, the image quality may be improved by counteracting the low-pass filtering that occurs when the signals for the navigator images are being acquired. As mentioned above, the weights applied to the signals to counteract the low-pass filtering effect may be coil-independent weights (obtained by knowing the characteristics of the bSSFP ramp used to acquire the navigator images).

Two techniques for improving the image quality by removing or reducing signals received from coils that are outside of or far from the user-defined region of interest, or from features which obscure the image, are now described.

One technique for determining how to weight the signal contributions from each coil may comprise knowing a coil geometry of the plurality of coils of the MRI apparatus. Thus, determining a weighted contribution of each coil may comprise: obtaining a coil geometry of the plurality of coils; determining, using the coil geometry, a distance of each coil from the region of interest; and assigning a weight to each coil based on the determined distance of each coil from the region of interest. The region of interest may be defined by a set of coordinates, and these may be mapped to the coil geometry to determine which coils are within the region of interest, close to the region of interest or far from the region of interest. This may then be used to assign a weight to each coil based on the determined distance of each coil from the region of interest.

For example, a high weight may be assigned to each coil which is close to the region of interest, because a signal received from a coil that is in or close to the region of interest may be desirable to generate an accurate representation of a target object in the region. Similarly, a low weight may be assigned to each coil which is further away from the region of interest, because a signal received from a coil that is further away from the region of interest may obscure the target object.

Alternatively, determining a weighted contribution of each coil may comprise: performing a prescan, using the MRI apparatus, over at least the region of interest of the body; determining, using the prescan, a coil sensitivity or coil sensitivity profile of each coil in the region of interest; and assigning a weight to each coil based on the determined coil sensitivity. The step of determining a coil sensitivity of each coil in the region of interest may comprise: assigning a high sensitivity to each coil which produces a bright image in the prescan of the region of interest; and assigning a low sensitivity to each coil which produces a dim image in the prescan of the region of interest. A high weight may be assigned to each high sensitivity coil in the region of interest, and a low weight may be assigned to each low sensitivity coil in the region of interest.

The coil geometries and/or the coil sensitivity profiles may be stored in storage or database. That is, once the coil geometries and/or sensitivity profiles have been obtained, they may be stored for subsequent use. The coil sensitivities may change over time, and therefore, it may be desirable to regularly redetermine the coil sensitivities and update the stored information in a storage/database. Alternatively, it may be desirable to determine the coil sensitivity each time an MRI scan is to be performed, as the coil sensitivities may depend on the region of interest.

At step S106, a navigator image of the region of interest is generated using the weighted combination of the signals received by each coil during the scanning step. The generation of the navigator image of the region of interest may be performed in real-time during the scanning step (S102), in an instance when the weighted contribution of each coil is known prior to the scanning. For example, if the prescan is performed ahead of the main MRI scan, the weighted contributions may also be determined before the main MRI scan, such that the signals received during the main MRI scan may be combined in real-time using the known weighted contributions. Similarly, if the coil geometry is known, the weighted contributions may also be known, and therefore, the signals received during the main MRI scan may be combined in real-time using the known weighted contributions. Alternatively, generating the MRI image of the region of interest may be performed after the scanning step is complete. In this case, the weighted contributions of each coil may be used to perform a weighted contribution of the signals received during the main MRI scan after the scanning step is complete.

As mentioned above, step S104 may further comprise applying weights that improve navigator image quality by counteracting the low-pass filtering that occurs when the signals for the navigator images are being acquired, that is, by counteracting the effect of the variable flip angles that are applied during the bSSFP ramp used to acquire the navigator signals.

In some cases, at step S104, a first set of weights that remove any unwanted signal may be performed first, and then a second set of weights may be applied to the remaining signals to counteract the variable flip angles/low-pass filtering effect. Alternatively, the first and second set of weights may be combined into a single set of weights that are applied at step S104.

FIG. 2A shows an example MRI navigator image 10 produced using a sum-of-squares combination of all the coils of an MRI apparatus. A region of interest 102 around a target object, in this case a heart, is shown. The target object in the region of interest 102 is difficult to see clearly, and other objects in the image 10 are equally as bright and obscure the target object.

Figure 2B:
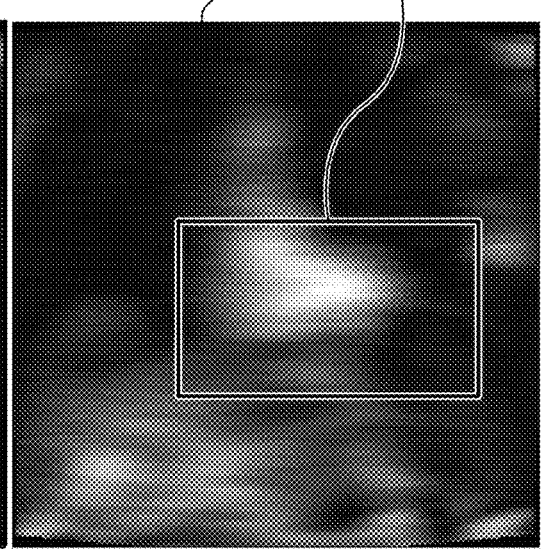
FIG. 2B shows an example MRI navigator image produced using weighted combinations of all the coils relative to a target region of interest.

FIG. 2B shows an example MRI navigator image 100 produced using weighted combinations of all the coils relative to a target region of interest, that is, by removing or reducing the impact of any unwanted signals when generating the navigator image (by applying coil-dependent weights that may be based on coil sensitivity or coil geometry). In this case, the target object is more clearly depicted in the region of interest 102, which enables improved tracking of the motion of the heart during respiration.

Figure 2C:
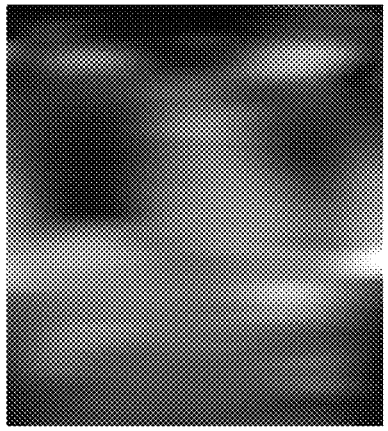
FIG. 2C shows a low-pass filtered image created by acquiring navigator images during a bSSFP ramp.

FIG. 2C shows a low-pass filtered image created by acquiring navigator images during a bSSFP ramp. The navigator image may be constructed from signals obtained during a prescan that may comprise applying ramp-up preparation pulses for a balanced steady-state free precession (bSSFP) scan. The low resolution navigator image of at least the region of interest may be obtained/constructed by combining the signals received from all of the coils of the MRI apparatus. The low resolution navigator image may be a one-dimensional image (in which case, there is no low-pass filtering effect) or a two-dimensional image or a three-dimensional image. Once the low resolution navigator image has been constructed, a low-pass filtered image is created (as shown in FIG. 2C). However, this image does not clearly depict the target object, because the low-pass filtering attenuates high frequencies (edges) so that the image appears blurred. due to the removal of certain lower frequency signals when the coil signals are combined. However, the weights which are applied to the signal contributions of each coil when generating the main MRI image may be selected to remove the low-pass filtering effect.

Figure 2D:
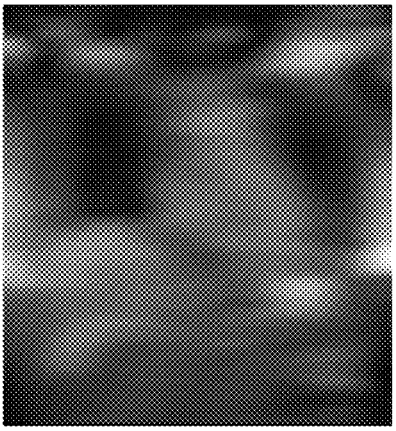
FIG. 2D shows the removal of the low-pass filtering effect in the image of FIG. 2C.

FIG. 2D shows the removal of the low-pass filtering effect in the image of FIG. 2C, by selecting and applying appropriate weights to the signal contributions of each coil when combining the signals to generate the MRI image. That is, the navigator image shown here is generated by applying coil-independent weights that reverse or remove the low-pass filtering by removing or reverting the bSSFP ramp during reconstruction. The weights may be chosen based on properties of the ramp itself. For example, the weights may be chosen to perform linear rescaling if the ramp was linear. It can be seen from FIG. 2D that certain features of the target object are more clearly visible in this image compared to the image of FIG. 2C.

Figure 2E:
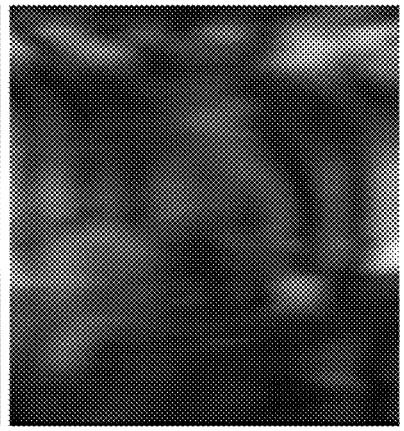
FIG. 2E shows the reversal of the low-pass filtering effect in the image of FIG. 2C.

FIG. 2E shows the reversal of the low-pass filtering effect in the image of FIG. 2C. In some cases, it may be desirable to choose weights to not just remove, but reverse the initial low-pass filtering modulation to produce a high-pass filtering effect instead. The step of assigning a weight to each coil based on the determined coil sensitivity may therefore comprise applying a weight which reverses the low-pass filtering when generating the navigator image of the region of interest, thereby generating a high-pass filtered navigator image. This technique may produce an improvement in edge detection in the navigator image, which may lead to significantly better motion tracking, particularly in the left-hand direction. FIG. 2E shows the result of reversing or inverting the bSSFP ramp profile to effectively apply a high-pass filter to the signals when performing the weighted combination of the coils to generate the navigator image. Additional details/ features of the target object are more visible in the image of FIG. 2E relative to FIG. 2C and FIG. 2D.

Figure 3:
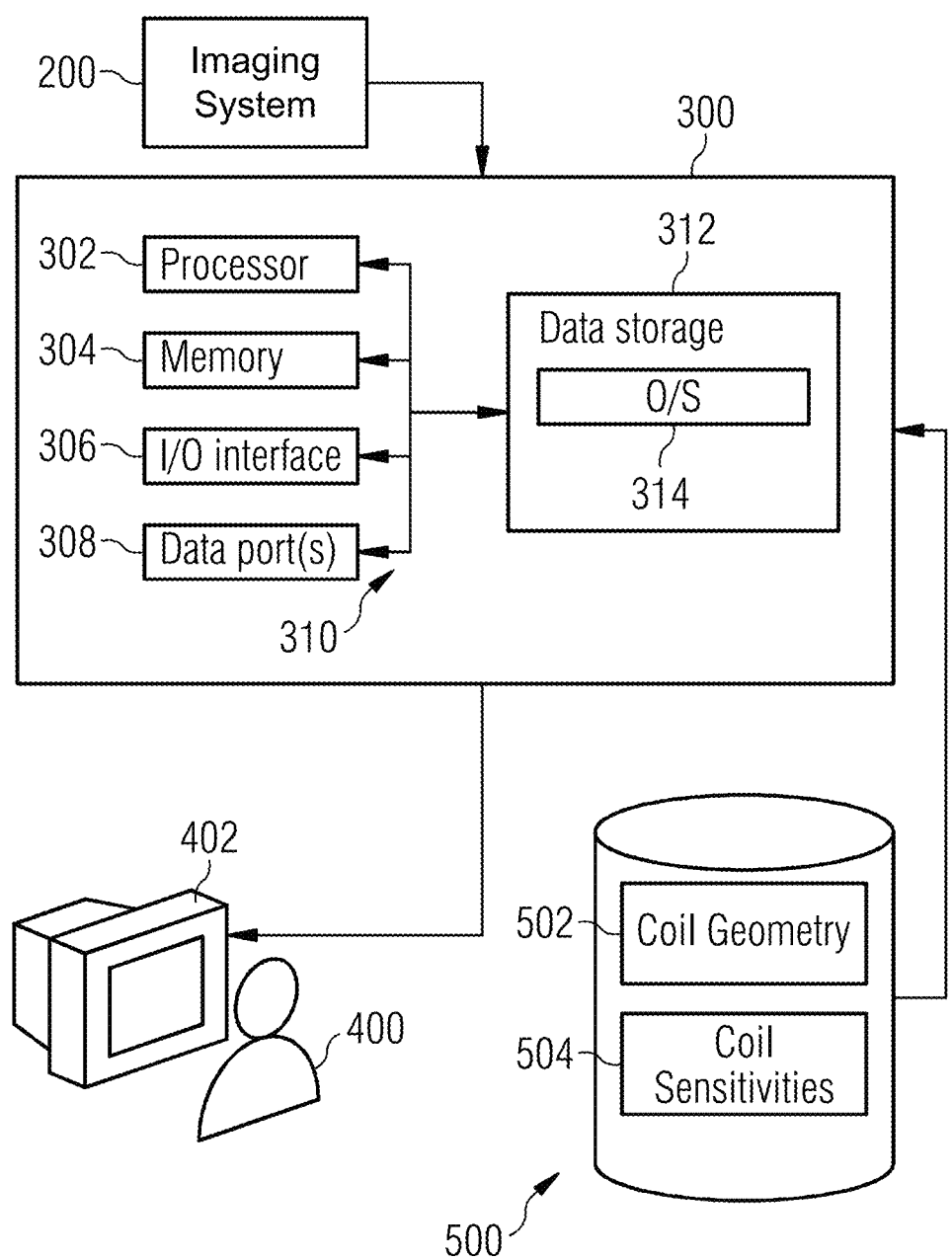
FIG. 3 is a block diagram of components which may be used to carry out the methods described herein.

FIG. 3 is a block diagram of components of an image processing system which may be used to carry out the methods described herein. The system comprises an image processor 300 which may perform the method of FIG. 1. An imaging system 200, for example, an MRI scanner, captures image data or signals which can be used to generate an image. The image data or signals are sent to the image processor 300. The output of the image processing, for example, a generated navigator image, may be output to a user 400 via any suitable user interface 402, for example, a screen on a computer or other electronic device. The image processor 300 may also be connected to a database 500, which may store, for example, a coil geometry 502 and/or coil sensitivities 504.

The image processor 300 may be formed from one or more servers and the steps (or tasks) in FIG. 1 may be split across the one or more servers or the cloud. The image processor 300 may include one or more processors 302, one or more memory devices 304 (generically referred to herein as memory 304), one or more input/output ("I/O") interface(s) 306, one or more data ports 308, and data storage 312. The image processor 300 may further include one or more buses 310 that functionally couple various components of the image processor 300.

The data storage 312 may store one or more operating systems (O/S) 314; and one or more program modules, applications, engines, computer-executable code, scripts, or the like. Any of the components depicted as being stored in data storage 312 may include any combination of software, firmware, and/or hardware. The software and/or firmware may include computer-executable code, instructions, or the like that may be loaded into the memory 304 for execution by one or more of the processor(s) 302 to perform any of the operations described earlier in connection with correspondingly named engines.

The bus(es) 310 may include at least one of a system bus, a memory bus, an address bus, or a message bus, and may permit exchange of information (e.g., data (including computer-executable code), signalling, etc.) between various components of the image processor 300. The bus(es) 310 may include, without limitation, a memory bus or a memory controller, a peripheral bus, an accelerated graphics port, and so forth. The bus(es) 310 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 304 of the image processor 300 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 304 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 304 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 312 and/or the database 500 may include removable storage and/or non-removable storage including, but not limited to, magnetic storage, optical disk storage, and/or tape storage. The data storage 312 and/or the database 500 may provide non-volatile storage of computer-executable instructions and other data. The memory 304, the database 500 and the data storage 312, removable and/or non-removable, are examples of computer-readable storage media (CRSM).

The data storage 312 may store computer-executable code, instructions, or the like that may be loadable into the memory 304 and executable by the processor(s) 302 to cause the processor(s) 302 to perform or initiate various operations. The data storage 312 may additionally store data that may be copied to memory 304 for use by the processor(s) 302 during the execution of the computer-executable instructions. Moreover, output data generated as a result of execution of the computer-executable instructions by the processor(s) 302 may be stored initially in memory 304, and may ultimately be copied to data storage 312 for non-volatile storage.

The data storage 312 may further store various types of data utilized by components of the image processor 300. Any data stored in the data storage 312 may be loaded into the memory 304 for use by the processor(s) 302 in executing computer-executable code. In addition, any data depicted as being stored in the data storage 312 may potentially be stored in one or more of the datastores and may be accessed and loaded in the memory 304 for use by the processor(s) 302 in executing computer-executable code.

The processor(s) 302 may be configured to access the memory 304 and execute computer-executable instructions loaded therein. For example, the processor(s) 302 may be configured to execute computer-executable instructions of the various program modules, applications, engines, or the like of the system to cause or facilitate various operations to be performed in accordance with one or more embodiments of the disclosure. The processor(s) 302 may include any suitable processing unit capable of accepting data as input, processing the input data in accordance with stored computer-executable instructions, and generating output data. The processor(s) 302 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 302 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 302 may be capable of supporting any of a variety of instruction sets.

Referring now to other illustrative components depicted as being stored in the data storage 312, the O/S 314 may be loaded from the data storage 312 into the memory 304 and may provide an interface between other application software executing on the image processor 300 and hardware resources of the image processor 300. More specifically, the O/S 314 may include a set of computer-executable instructions for managing hardware resources of the system and for providing common services to other application programs (e.g., managing memory allocation among various application programs). In certain example embodiments, the O/S 314 may control execution of one or more of the program modules depicted as being stored in the data storage 312. The O/S 314 may include any operating system now known or which may be developed in the future including, but not limited to, any server operating system, any mainframe operating system, or any other proprietary or non-proprietary operating system.

Referring now to other illustrative components of the image processor 300, the input/output (I/O) interface(s) 306 may facilitate the receipt of input information by the image processor 300 from one or more I/O devices as well as the output of information from the image processor 300 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the image processor 300 or may be separate. The I/O devices may further include, for example, any number of peripheral devices such as data storage devices, printing devices, and so forth.

The I/O interface(s) 306 may also include an interface for an external peripheral device connection such as universal serial bus (USB), FireWire, Thunderbolt, Ethernet port or other connection protocol that may connect to one or more networks. The I/O interface(s) 306 may also include a connection to one or more antennas to connect to one or more networks via a wireless local area network (WLAN) (such as Wi-Fi) radio, Bluetooth, and/or a wireless network radio, such as a radio capable of communication with a wireless communication network such as a Long Term Evolution (LTE) network, WiMAX network, 3G network, etc.

The image processor 300 may further include one or more data ports 310 via which the image processor 300 may communicate with any of the processing modules. The data ports(s) 310 may enable communication with the image capture device 200 and the database 500.

It should be appreciated that the engines and the program modules depicted in the Figures are merely illustrative and not exhaustive and that processing described as being supported by any particular engine or module may alternatively be distributed across multiple engines, modules, or the like, or performed by a different engine, module, or the like. In addition, various program module(s), script(s), plug-in(s), Application Programming Interface(s) (API(s)), or any other suitable computer-executable code hosted locally on the system and/or hosted on other computing device(s) accessible via one or more of the network(s), may be provided to support the provided functionality, and/or additional or alternate functionality. Further, functionality may be modularized differently such that processing described as being supported collectively by the collection of engines or the collection of program modules may be performed by a fewer or greater number of engines or program modules, or functionality described as being supported by any particular engine or module may be supported, at least in part, by another engine or program module. In addition, engines or program modules that support the functionality described herein may form part of one or more applications executable across any number of devices of the system in accordance with any suitable computing model such as, for example, a client-server model, a peer-to-peer model, and so forth. In addition, any of the functionality described as being supported by any of the engines or program modules may be implemented, at least partially, in hardware and/or firmware across any number of devices.

It should further be appreciated that the system may include alternate and/or additional hardware, software, or firmware components beyond those described or depicted without departing from the scope of the disclosure. More particularly, it should be appreciated that software, firmware, or hardware components depicted as forming part of the system are merely illustrative and that some components may not be present or additional components may be provided in various embodiments. While various illustrative engines have been depicted and described as software engines or program modules, it should be appreciated that functionality described as being supported by the engines or modules may be enabled by any combination of hardware, software, and/or firmware. It should further be appreciated that each of the above-mentioned engines or modules may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular engine or module may, in various embodiments, be provided at least in part by one or more other engines or modules. Further, one or more depicted engines or modules may not be present in certain embodiments, while in other embodiments, additional engines or modules not depicted may be present and may support at least a portion of the described functionality and/or additional functionality. Moreover, while certain engines modules may be depicted or described as sub-engines or sub-modules of another engine or module, in certain embodiments, such engines or modules may be provided as independent engines or modules or as sub-engines or sub-modules of other engines or modules.

The operations described and depicted in the illustrative methods of FIG. 1 may be carried out or performed in any suitable order as desired in various example embodiments of the disclosure. Additionally, in certain example embodiments, at least a portion of the operations may be carried out in parallel. Furthermore, in certain example embodiments, less, more, or different operations than those depicted in FIG. 1 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular system, system component, device, or device component may be performed by any other system, device, or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Program modules, applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The invention claimed is:

1. A method of correcting for motion in magnetic resonance images during image acquisition using a magnetic resonance imaging (MRI) apparatus including a plurality of coils for receiving signals, the method comprising:
   receiving a user-defined region of interest of a body to be imaged;
   scanning, using the MRI apparatus, at least the region of interest of the body; and
   generating a navigator image of the region of interest by performing a weighted combination of a signal received by each of the plurality of coils during the scanning.

2. The method of imaging as claimed in claim 1, further comprising:
   determining a weighted contribution of each of the plurality of coils to an MRI image of the region of interest.

3. The method of imaging as claimed in claim 2, wherein the step of determining a weighted contribution of each of the plurality of coils comprises:
   obtaining a coil geometry of the plurality of coils;
   determining, using the coil geometry, a distance of each of the plurality of coils from the region of interest; and
   assigning a weight to each of the plurality of coils based on the determined distance of each of the plurality of coils from the region of interest.

4. The method of imaging as claimed in claim 3, wherein the step of assigning a weight to each of the plurality of coils based on the determined distance of each of the plurality of coils from the region of interest comprises:
   assigning a high weight to each of the plurality of coil which is close to the region of interest; and
   assigning a low weight to each of the plurality of coils which is further away from the region of interest.

5. The method of imaging as claimed in claim 2, wherein the step of determining a weighted contribution of each of the plurality of coils comprises:
   performing a prescan, using the MRI apparatus, over at least the region of interest of the body;
   determining, using the prescan, a coil sensitivity of each of the plurality of coils in the region of interest; and
   assigning a weight to each of the plurality of coils based on the determined coil sensitivity.

6. The method of imaging as claimed in claim 5, wherein the step of determining a coil sensitivity of each of the plurality of coils in the region of interest comprises:
   assigning a high sensitivity to each of the plurality of coils which produces a bright image in the prescan of the region of interest; and
   assigning a low sensitivity to each of the plurality of coils which produces a dim image in the prescan of the region of interest.

7. The method of imaging as claimed in claim 6, wherein the step of assigning a weight to each of the plurality of coils based on the determined coil sensitivity in the region of interest comprises:

assigning a high weight to each high sensitivity coil in the region of interest; and assigning a low weight to each low sensitivity coil in the region of interest.

8. The method of imaging as claimed in claim 2, wherein the step of generating a navigator image of the region of interest is performed in real-time during the scan, in an instance when the weighted contribution of each of the plurality of coils is known prior to the scanning.

9. The method of imaging as claimed in claim 2, wherein the step of generating a navigator image of the region of interest is performed after the scanning is complete.

10. The method of imaging as claimed in claim 1, wherein the step of performing a weighted combination of a signal received by each of the plurality of coils during the scanning comprises performing a weighted combination of signals using a first set of weights to remove any unwanted signals when generating the navigator image.

11. The method of imaging as claimed in claim 1, wherein the step of scanning comprises:

applying ramp-up preparation pulses for a balanced steady-state free precession scan; and obtaining low resolution navigator images of at least the region of interest while the ramp-up preparation pulses are applied.

12. The method of imaging as claimed in claim 10, wherein the low resolution navigator images are low-pass filtered images, and the step of performing a weighted combination of a signal comprises performing a weighted combination of signals using a second set of weights to remove low-pass filtering when generating the navigator image.

13. The method of imaging as claimed in claim 12, wherein the step of performing the weighted combination of signals comprises performing a weighted combination of signals using a third set of weights to reverse the low-pass filtering when generating the navigator image of the region of interest, thereby generating a high-pass filtered navigator image.

14. A computer readable medium carrying processor control code which when implemented in a system causes the system to carry out the method of claim 1.

15. An image processing system, comprising an image capture device which is configured to capture an image;

an image processor which is configured to receive an image from the image capture device and carry out the method of claim 1, and a user interface which is configured to display an output result generated by the image processor.

* * * * *